(12) United States Patent
Lai et al.

(10) Patent No.: US 7,883,686 B2
(45) Date of Patent: Feb. 8, 2011

(54) MCM-22 FAMILY MOLECULAR SIEVE COMPOSITION, ITS METHOD OF MAKING, AND USE FOR HYDROCARBON CONVERSIONS

(75) Inventors: Wenyih Frank Lai, Bridgewater, NJ (US); Robert Ellis Kay, Easton, PA (US); Mohan Kalyanaraman, Media, PA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 792 days.

(21) Appl. No.: 11/823,722

(22) Filed: Jun. 28, 2007

(65) Prior Publication Data
US 2008/0027260 A1    Jan. 31, 2008

Related U.S. Application Data

(60) Provisional application No. 60/834,010, filed on Jul. 28, 2006, provisional application No. 60/834,115, filed on Jul. 28, 2006.

(51) Int. Cl.
*C01B 39/48* (2006.01)
*C01B 39/46* (2006.01)
*C10G 11/05* (2006.01)
*C10G 47/16* (2006.01)
*C10G 49/08* (2006.01)
*C10G 25/03* (2006.01)
*C07C 7/13* (2006.01)

(52) U.S. Cl. .................. 423/700; 423/705; 423/706; 423/709; 423/718; 208/111.01; 208/111.15; 208/136; 208/143; 208/310 Z

(58) Field of Classification Search ............... 423/700, 423/705, 709, 706, 718; 208/46, 110.01, 208/111.15, 136, 143, 301 Z
See application file for complete search history.

(56) References Cited

U.S. PATENT DOCUMENTS

| 4,439,409 | A | * | 3/1984 | Puppe et al. ............... 423/706 |
| 4,826,667 | A | | 5/1989 | Zones et al. |
| 4,954,325 | A | | 9/1990 | Rubin et al. |
| 5,107,047 | A | * | 4/1992 | Del Rossi et al. ........... 585/666 |
| 5,236,575 | A | | 8/1993 | Bennett et al. |
| 5,250,277 | A | | 10/1993 | Kresge et al. |
| 5,362,697 | A | | 11/1994 | Fung et al. |

(Continued)

FOREIGN PATENT DOCUMENTS

EP    0 293 032    11/1988

(Continued)

OTHER PUBLICATIONS

U.S. Appl. No. 60/834,115, filed Jul. 28, 200, Lai, et al.

(Continued)

*Primary Examiner*—David M Brunsman
(74) *Attorney, Agent, or Firm*—Darryl M. Tyus; Xiaobing Feng

(57) ABSTRACT

This disclosure relates to a crystalline MCM-22 family molecular sieve having a platelet aggregates morphology wherein greater than 50 wt % of the molecular sieve having a crystal diameter greater than 1 μm as measured by the SEM. The crystalline MCM-22 family molecular sieve of this disclosure, wherein the platelet aggregates morphology is rosette habit morphology, or multiple layer plate's morphology.

24 Claims, 12 Drawing Sheets

XRD of As-synthesized Products of Example A (Comparative)

U.S. PATENT DOCUMENTS

| | | | |
|---|---|---|---|
| 6,077,498 | A | 6/2000 | Diaz Cabanas et al. |
| 6,936,744 | B1 | 8/2005 | Cheng et al. |
| 2006/0217580 | A1* | 9/2006 | Kuechler et al. ............ 585/533 |

FOREIGN PATENT DOCUMENTS

| | | |
|---|---|---|
| WO | WO 97/17290 | 5/1997 |
| WO | WO 01/21562 | 3/2001 |
| WO | WO 2005/118476 | 12/2005 |
| WO | WO 2006/094006 | 9/2006 |
| WO | WO 2007/094937 | 8/2007 |
| WO | WO 2007/094938 | 8/2007 |

OTHER PUBLICATIONS

U.S. Appl. No. 60/834,010, filed Jul. 28, 2006, Lai, et al.

W. Roth, et al., "MCM-22 zeolite family and the delaminated zeolite MCM-56 obtained in one-step synthesis", *Studies in Surface Science Catalysis*, vol. 158, p. 19 (2005).

U.S. Appl. No. 60/834,030, filed Jul. 28, 2006, Roth, et al.

U.S. Appl. No. 60/834,001, filed Jul. 28, 2006, Roth, et al.

U.S. Appl. No. 60/834,032, filed Jul. 28, 2006, Roth, et al.

U.S. Appl. No. 60/834,031, filed Jul. 28, 2006, Roth, et al.

U.S. Appl. No. 60/926,204, filed Apr. 25, 2007, Roth, et al.

S. H. Lee, et al., *Chemistry Letters*, vol. 32, No. 6, p. 542-543 (2003).

S. H. Lee, et al., "Reinvestigation into the synthesis of zeolites using diquaternary alkylammonium ions $(CH_3)_3N^+(CH_2)_nN^+(CH_3)_3$ with n=3-10 as structure-directing agents", *Microporous and Mesoporous Materials*, vol. 68, p, 97-104 (2004).

* cited by examiner

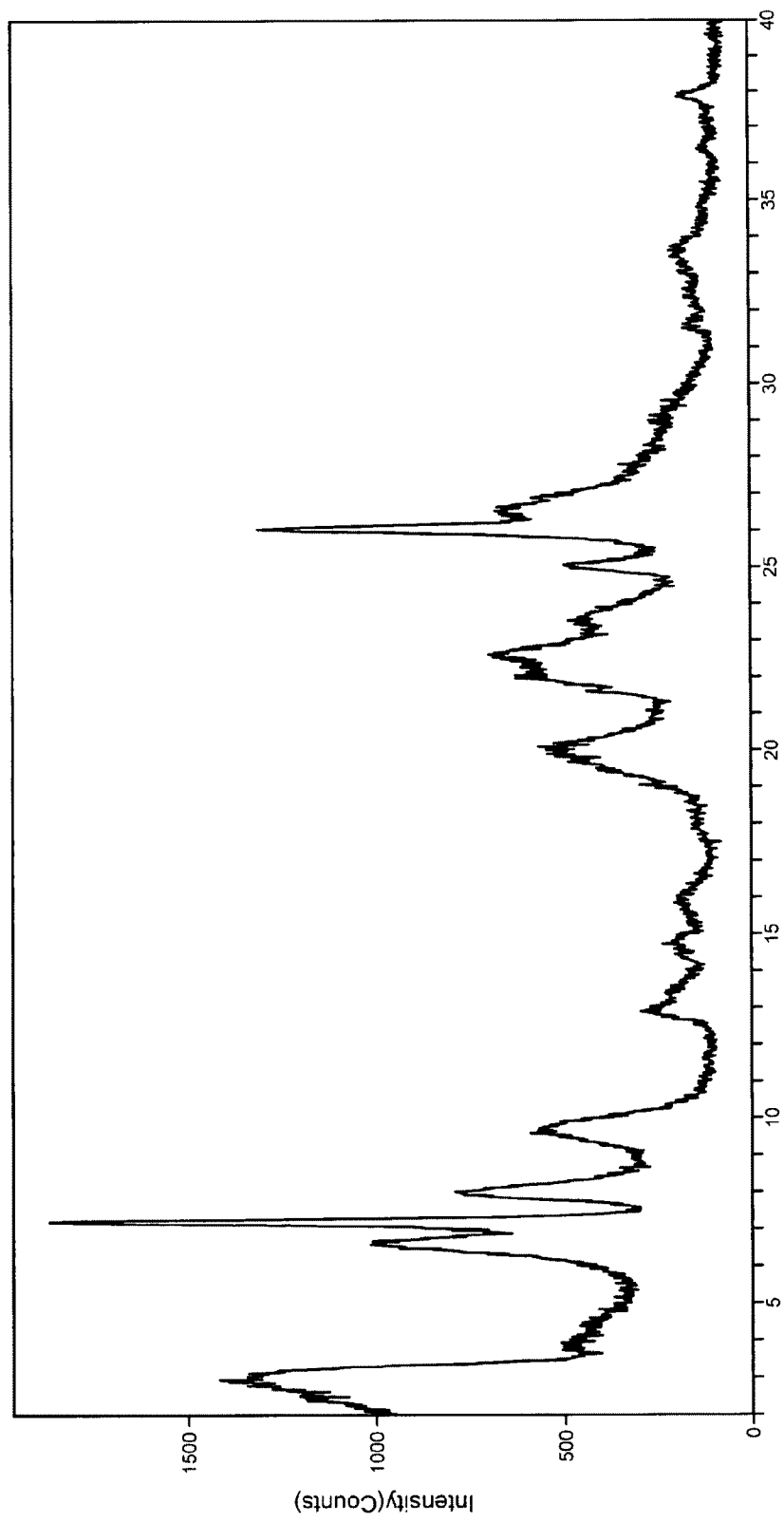
Figure 1: XRD of As-synthesized Products of Example A (Comparative)

Figure 2: SEM of Example A (Comparative)

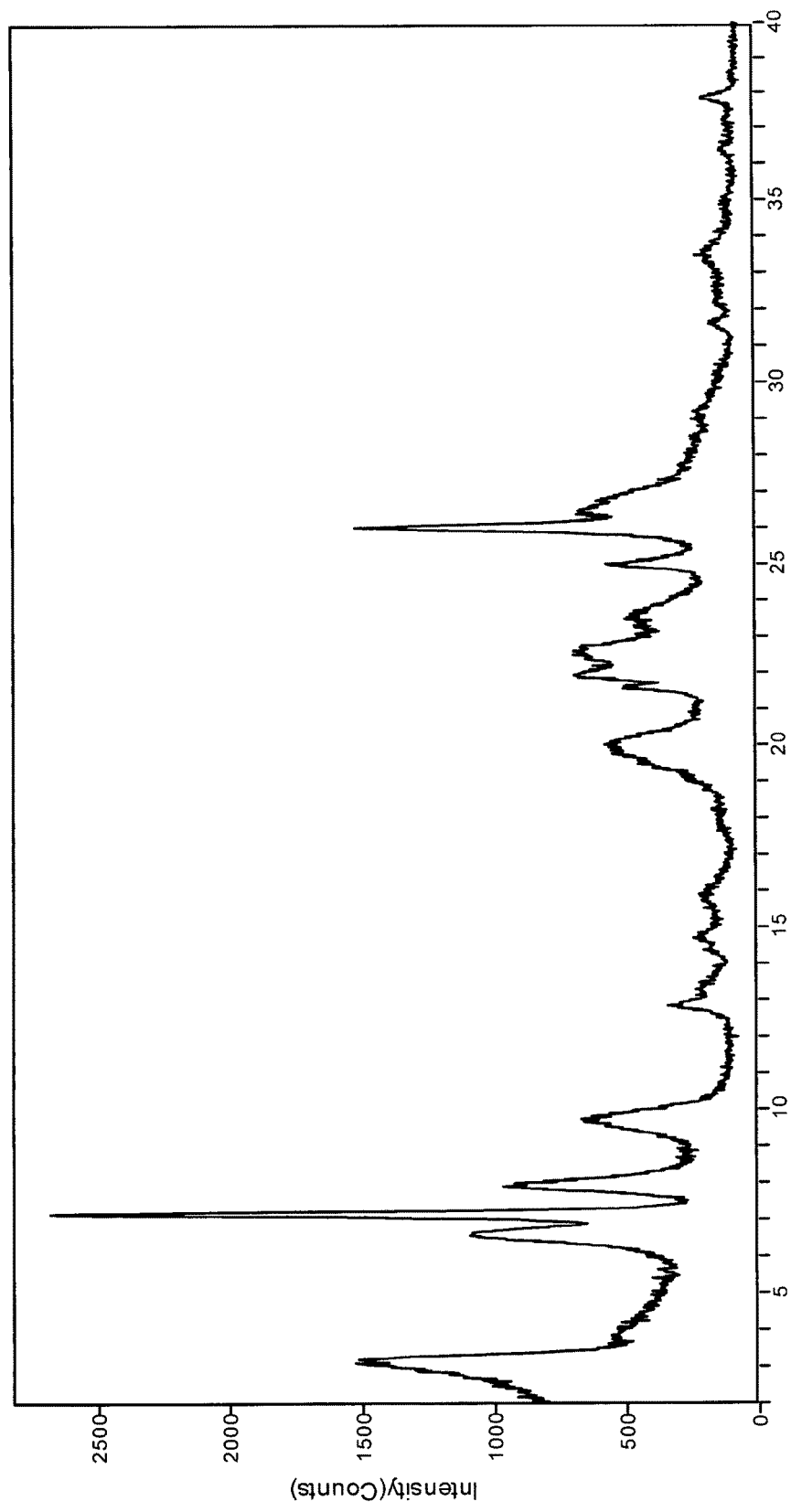
Figure 3A: XRD of the as-synthesized product of example 1 after 120 hrs of crystallization

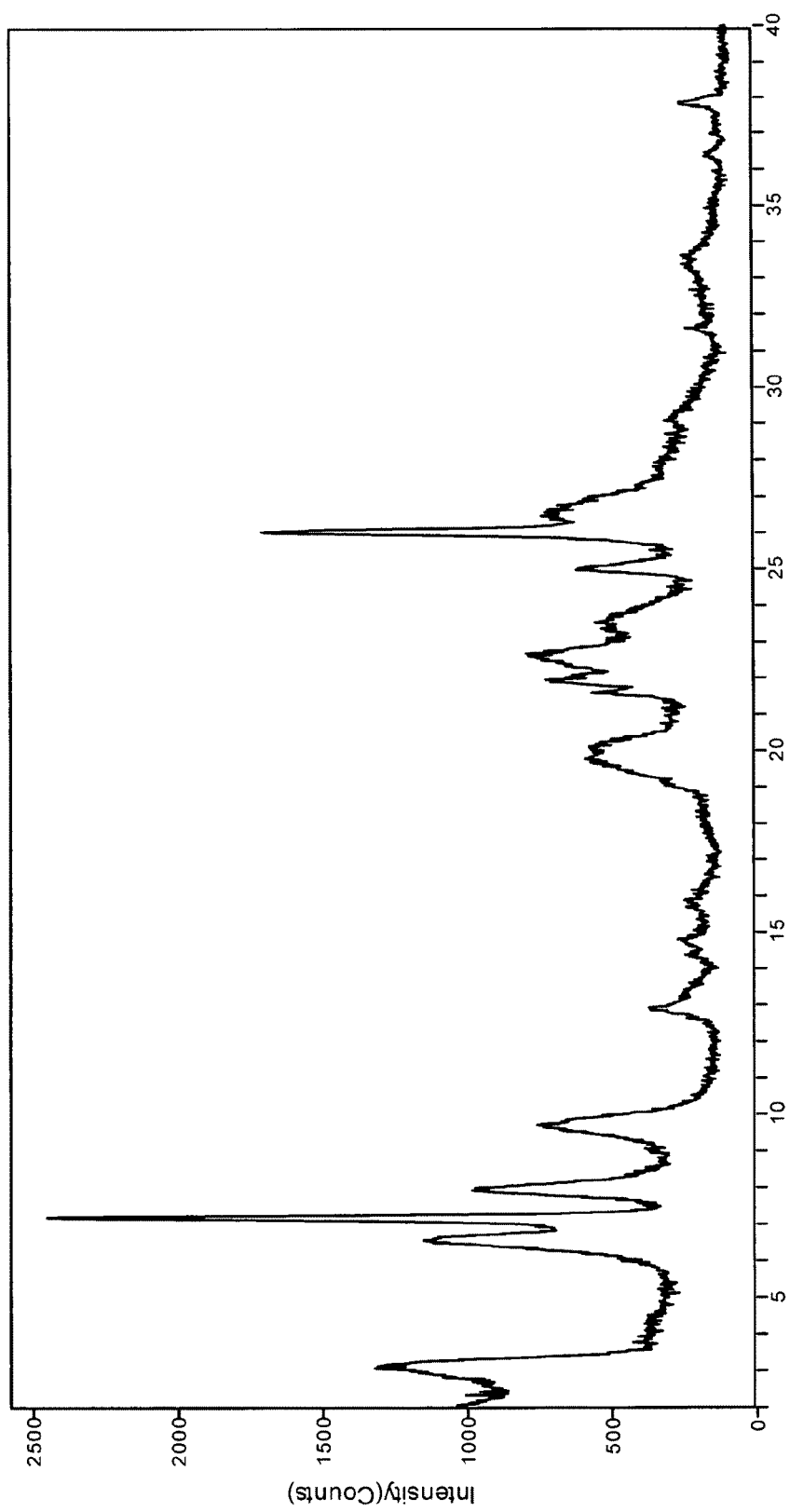
Figure 3B: XRD of the as-synthesized product of example 1 after 168 hrs of crystallization

Figure 4: SEM of the as-synthesized product of example 1 after 168 hrs of crystallization

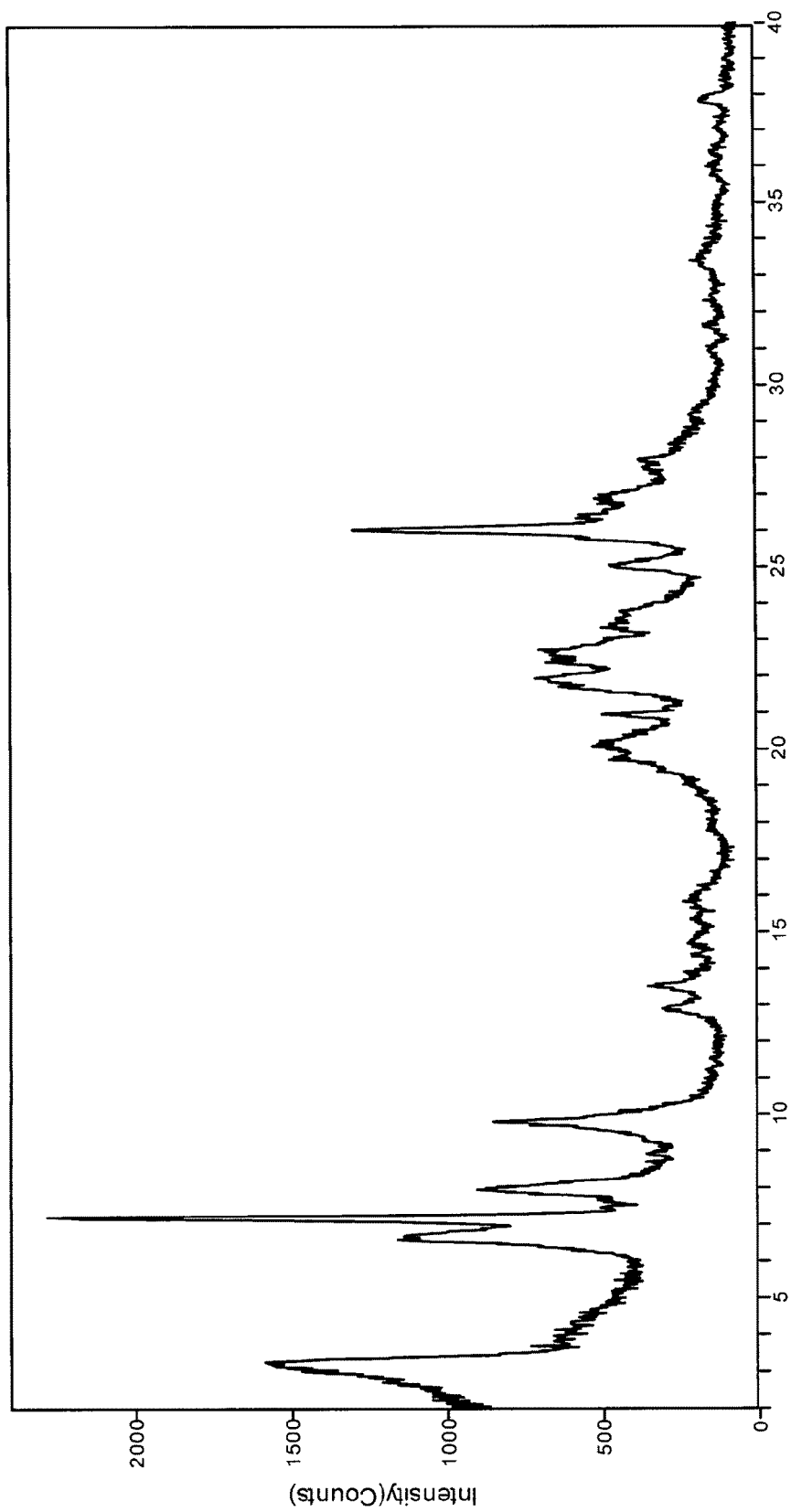
Figure 5: XRD of the as-synthesized product of example 2 after 216 hrs of crystallization

Figure 6A: SEM of the as-synthesised product of example 2 after 216 hrs of crystallization

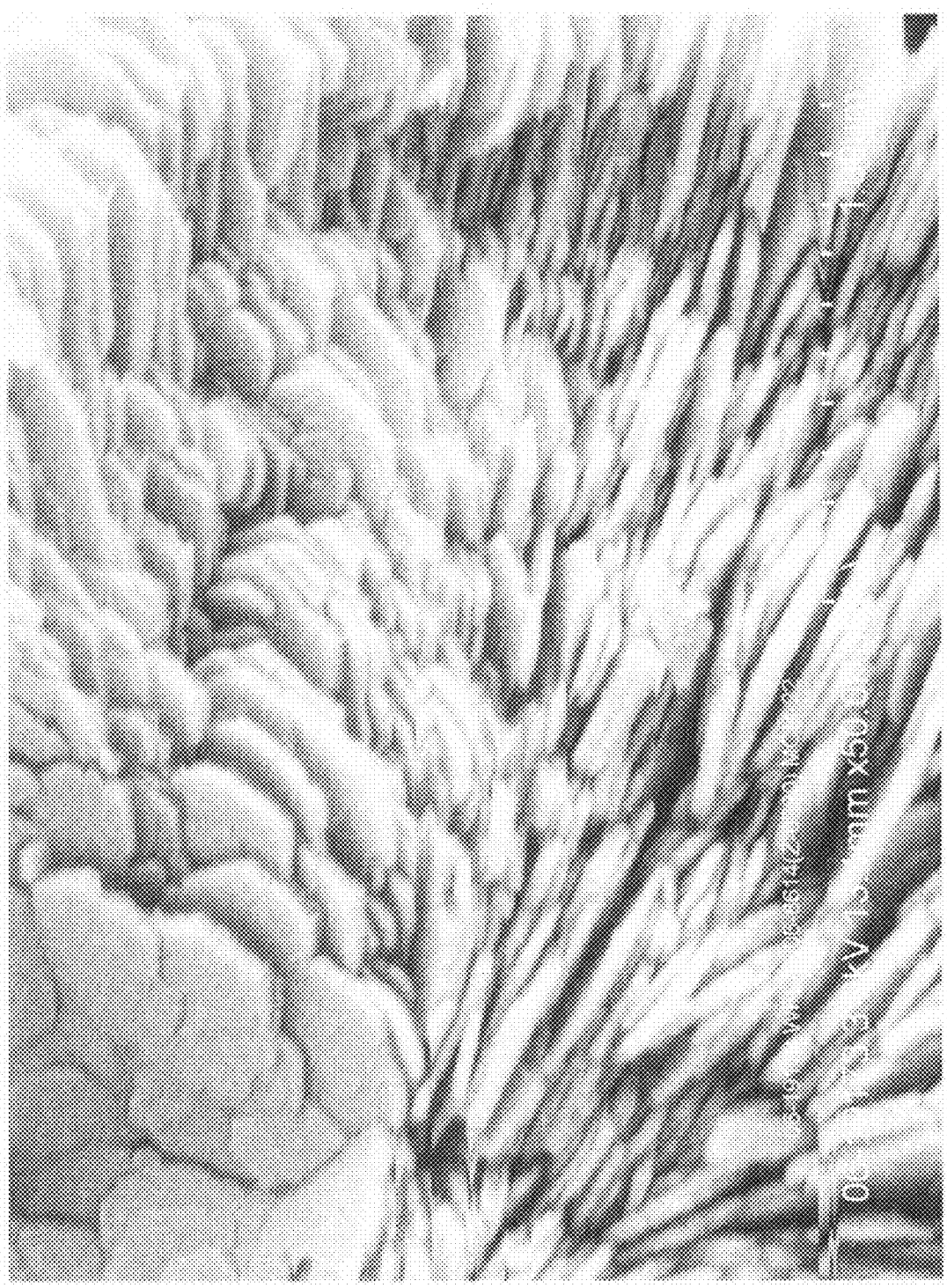
Figure 6B: SEM of the as-synthesized product of example 2 after 216 hrs of crystallization

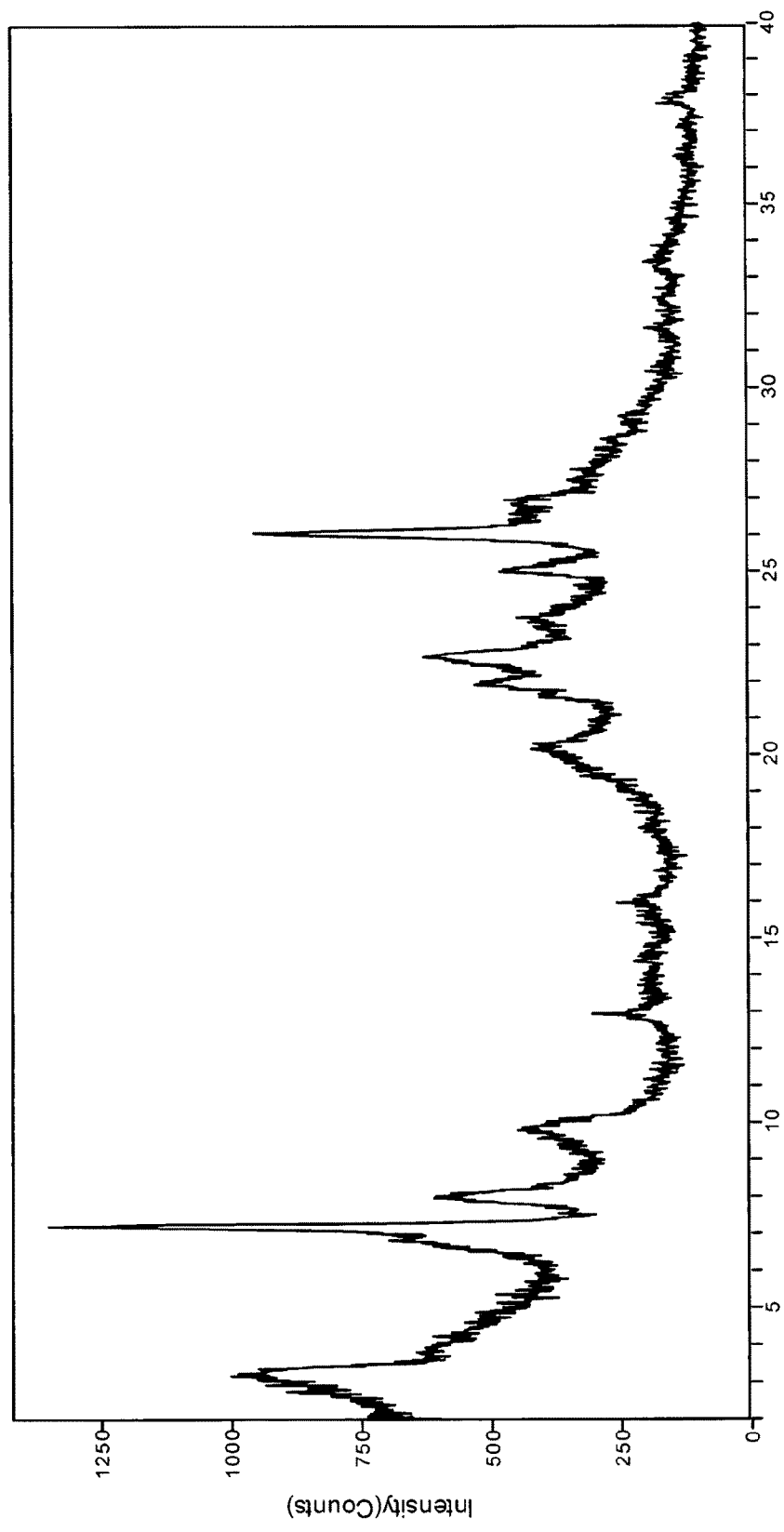
Figure 7: XRD of the as-synthesized product of example 3 after 48 hrs of crystallization

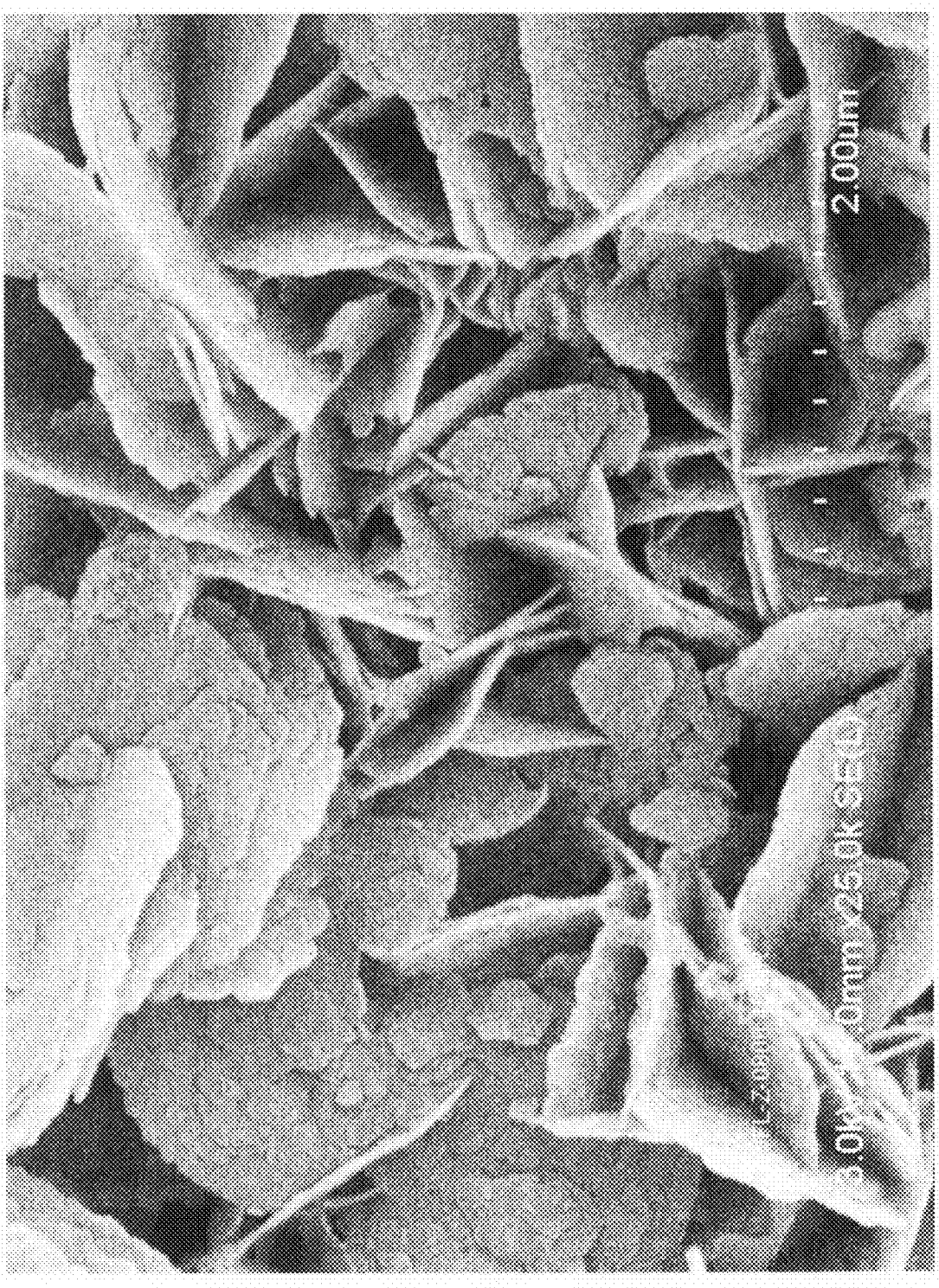
Figure 8: SEM of the as-synthesized product of example 3 after 48 hrs of crystallization

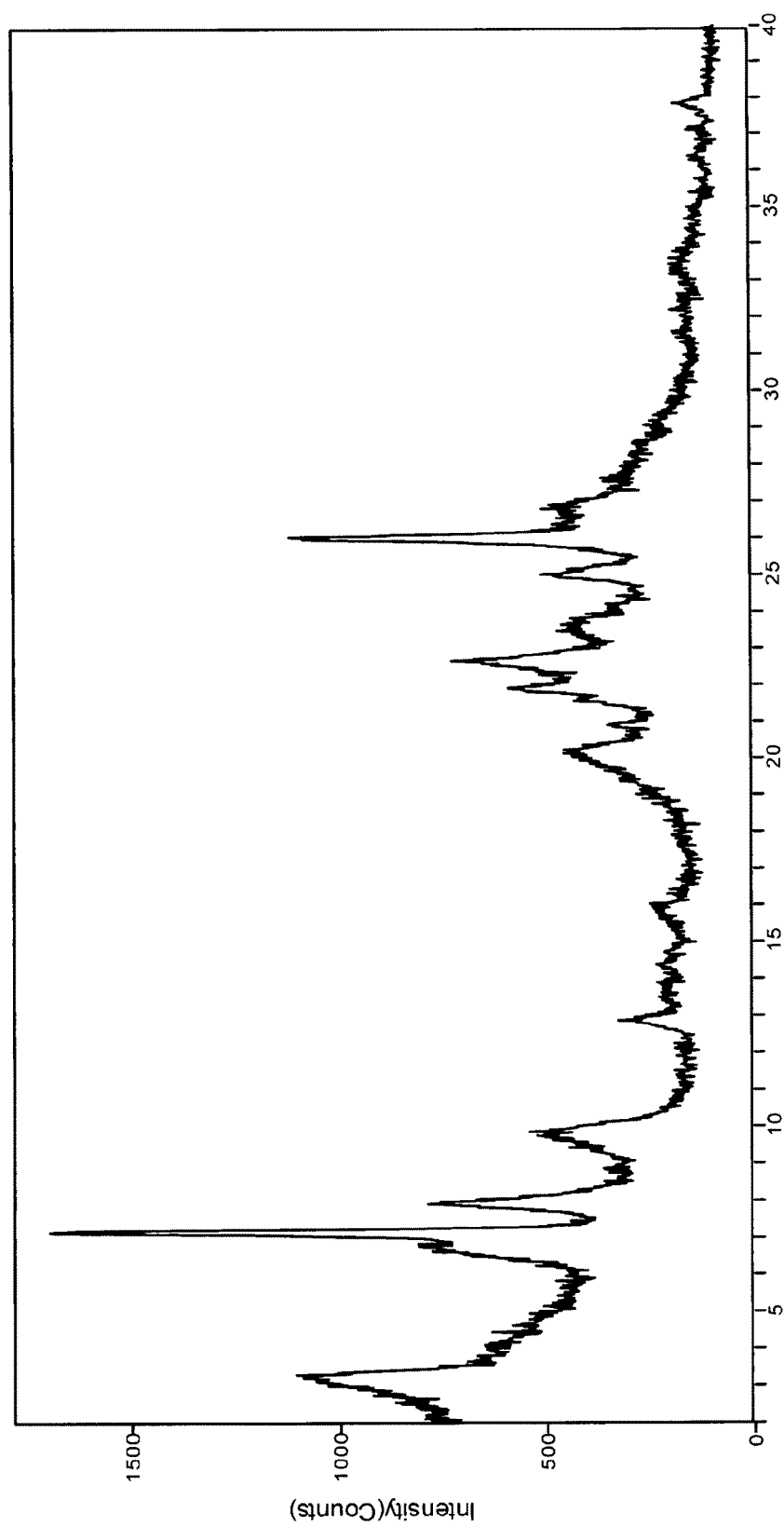
Figure 9: XRD of the as-synthesized product of example 4 after 48 hrs of crystallization

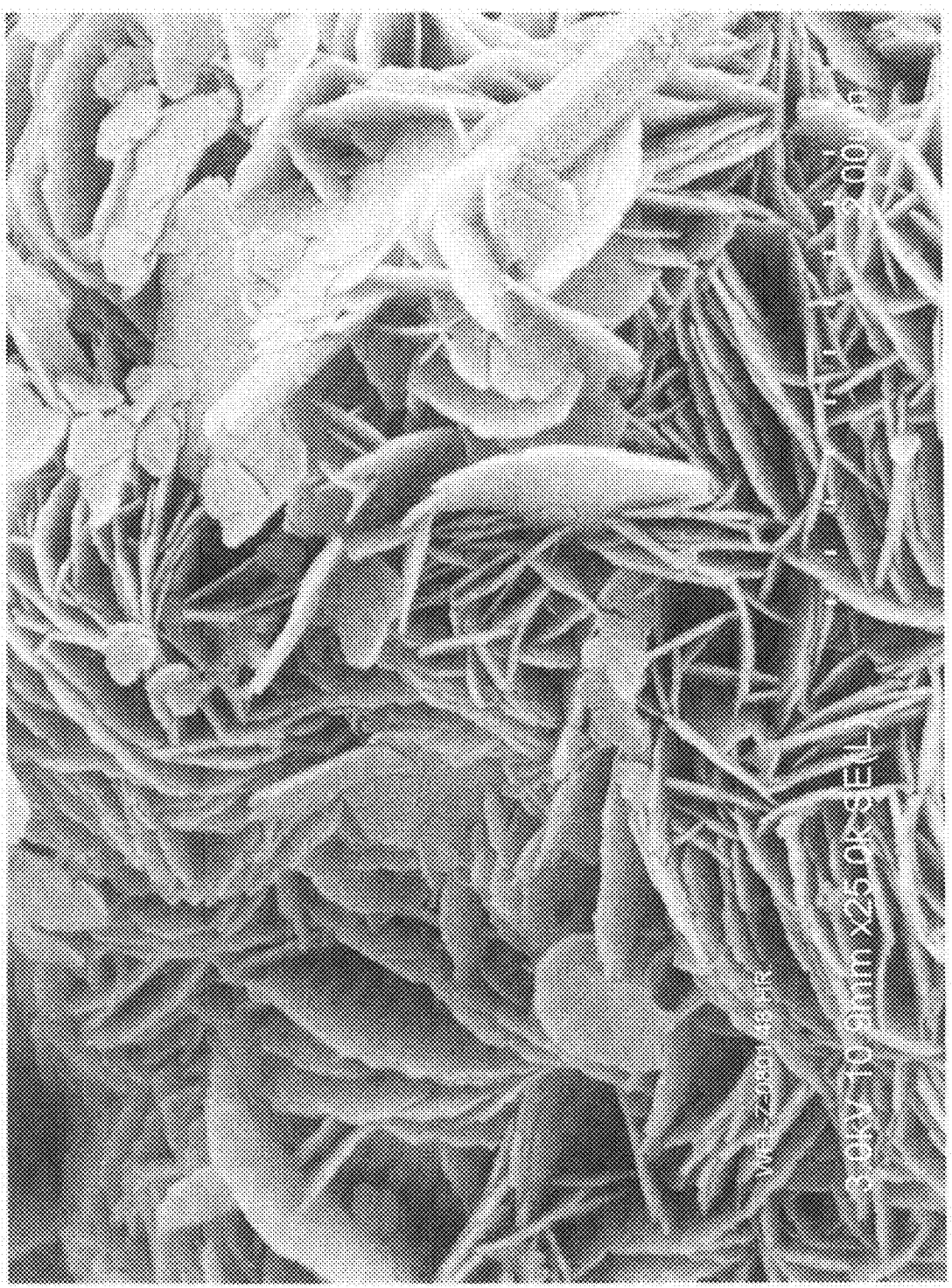
Figure 10: SEM of the as-synthesized product of example 4 after 48 hrs of crystallization

MCM-22 FAMILY MOLECULAR SIEVE COMPOSITION, ITS METHOD OF MAKING, AND USE FOR HYDROCARBON CONVERSIONS

CROSS REFERENCE TO RELATED APPLICATIONS

This application claims benefit of U.S. Provisional Patent Application No. 60/834,010, filed Jul. 28, 2006, and U.S. Provisional Patent Application No. 60/834,115, filed Jul. 28, 2006, the references of which are incorporated herein.

FIELD OF THE INVENTION

This invention relates to a novel MCM-22 family molecular sieve composition, a method of making thereof and the use thereof for hydrocarbon conversions. In particular, this invention relates to a novel MCM-22 family molecular sieve composition comprising greater than 50 wt % of the molecular sieve having a crystal diameter greater than 1 μm as measured by the SEM, a method of making thereof and the use thereof for hydrocarbon conversions.

BACKGROUND OF THIS DISCLOSURE

Molecular sieve materials, both natural and synthetic, have been demonstrated in the past to have catalytic properties for various types of hydrocarbon conversion. Certain molecular sieves, zeolites, AlPOs, mesoporous materials, are ordered, porous crystalline materials having a definite crystalline structure as determined by X-ray diffraction (XRD). Within the crystalline molecular sieve material there are a large number of cavities which may be interconnected by a number of channels or pores. These cavities and pores are uniform in size within a specific molecular sieve material. Because the dimensions of these pores are such as to accept for adsorption molecules of certain dimensions while rejecting those of larger dimensions, these materials have come to be known as "molecular sieves" and are utilized in a variety of industrial processes.

Such molecular sieves, both natural and synthetic, include a wide variety of positive ion-containing crystalline silicates. These silicates can be described as rigid three-dimensional framework of $SiO_4$ and Periodic Table Group 13 element oxide (e.g., $AlO_4$). The tetrahedra are cross-linked by the sharing of oxygen atoms whereby the ratio of the total Group 13 element (e.g., aluminum) and silicon atoms to oxygen atoms is 1:2. The electrovalence of the tetrahedra containing the Group 13 element (e.g., aluminum) is balanced by the inclusion in the crystal of a cation, for example a proton, an alkali metal or an alkaline earth metal cation. This can be expressed wherein the ratio of the Group 13 element (e.g., aluminum) to the number of various cations, such as $H^+$, $Ca^{2+}/2$, $Sr^{2+}/2$, $Na^+$, $K^+$, or $Li^+$, is equal to unity.

Molecular sieves that find application in catalysis include any of the naturally occurring or synthetic crystalline molecular sieves. Examples of these zeolites include large pore zeolites, intermediate pore size zeolites, and small pore zeolites. These zeolites and their isotypes are described in "Atlas of Zeolite Framework Types", eds. W. H. Meier, D. H. Olson and Ch. Baerlocher, Elsevier, Fifth Edition, 2001, which is hereby incorporated by reference. A large pore zeolite generally has a pore size of at least about 7 Å and includes LTL, VFI, MAZ, FAU, OFF, *BEA, and MOR framework type zeolites (IUPAC Commission of Zeolite Nomenclature). Examples of large pore zeolites include mazzite, offretite, zeolite L, VPI-5, zeolite Y, zeolite X, omega, and Beta. An intermediate pore size zeolite generally has a pore size from about 5 Å to less than about 7 Å and includes, for example, MFI, MEL, EUO, MTT, MFS, AEL, AFO, HEU, FER, MWW, and TON framework type zeolites (IUPAC Commission of Zeolite Nomenclature). Examples of intermediate pore size zeolites include ZSM-5, ZSM-11, ZSM-22, MCM-22, silicalite 1, and silicalite 2. A small pore size zeolite has a pore size from about 3 Å to less than about 5.0 Å and includes, for example, CHA, ER1, KFI, LEV, SOD, and LTA framework type zeolites (IUPAC Commission of Zeolite Nomenclature). Examples of small pore zeolites include ZK-4, ZSM-2, SAPO-34, SAPO-35, ZK-14, SAPO-42, ZK-21, ZK-22, ZK-5, ZK-20, zeolite A, chabazite, zeolite T, gmelinite, ALPO-17, and clinoptilolite.

U.S. Pat. No. 4,439,409 refers to a crystalline molecular sieve composition of matter named PSH-3 and its synthesis from a hydrothermal reaction mixture containing hexamethyleneimine, an organic compound which acts as directing agent for synthesis of the MCM-56 (U.S. Pat. No. 5,362,697). Hexamethyleneimine is also taught for use in synthesis of crystalline molecular sieves MCM-22 (U.S. Pat. No. 4,954,325) and MCM-49 (U.S. Pat. No. 5,236,575). A molecular sieve composition of matter referred to as zeolite SSZ-25 (U.S. Pat. No. 4,826,667) is synthesized from a hydrothermal reaction mixture containing an adamantane quaternary ammonium ion. U.S. Pat. No. 6,077,498 refers to a crystalline molecular sieve composition of matter named ITQ-1 and its synthesis from a hydrothermal reaction mixture containing one or a plurality of organic additives.

The term "MCM-22 family material" (or "material of the MCM-22 family" or "molecular sieve of the MCM-22 family"), as used herein, includes:

(i) molecular sieves made from a common first degree crystalline building block "unit cell having the MWW framework topology". A unit cell is a spatial arrangement of atoms which is tiled in three-dimensional space to describe the crystal as described in the "Atlas of Zeolite Framework Types", Fifth edition, 2001, the entire content of which is incorporated as reference;

(ii) molecular sieves made from a common second degree building block, a 2-dimensional tiling of such MWW framework type unit cells, forming a "monolayer of one unit cell thickness", preferably one c-unit cell thickness;

(iii) molecular sieves made from common second degree building blocks, "layers of one or more than one unit cell thickness", wherein the layer of more than one unit cell thickness is made from stacking, packing, or binding at least two monolayers of one unit cell thick of unit cells having the MWW framework topology. The stacking of such second degree building blocks can be in a regular fashion, an irregular fashion, a random fashion, or any combination thereof; or (iv) molecular sieves made by any regular or random 2-dimensional or 3-dimensional combination of unit cells having the MWW framework topology.

The MCM-22 family materials are characterized by having an X-ray diffraction pattern including d-spacing maxima at 12.4±0.25, 3.57±0.07 and 3.42±0.07 Angstroms (either calcined or as-synthesized). The MCM-22 family materials may also be characterized by having an X-ray diffraction pattern including d-spacing maxima at 12.4±0.25, 6.9±0.15, 3.57±0.07 and 3.42±0.07 Angstroms (either calcined or as-synthesized). The X-ray diffraction data used to characterize the molecular sieve are obtained by standard techniques using the K-alpha doublet of copper as the incident radiation and a diffractometer equipped with a scintillation counter and associated computer as the collection system. Materials belong to the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), ITQ-30 (described in International Patent Publication No. WO2005118476), MCM-36 (described in U.S. Pat. No. 5,250,277), MCM-49 (described in U.S. Pat. No. 5,236,575) and MCM-56 (described in U.S. Pat. No. 5,362,697). The entire contents of the patents are incorporated herein by reference.

It is to be appreciated the MCM-22 family molecular sieves described above are distinguished from conventional large pore zeolite alkylation catalysts, such as mordenite, in that the MCM-22 materials have 12-ring surface pockets which do not communicate with the 10-ring internal pore system of the molecular sieve.

The zeolitic materials designated by the IZA-SC as being of the MWW topology are multi-layered materials which have two pore systems arising from the presence of both 10 and 12 membered rings. The Atlas of Zeolite Framework Types classes five differently named materials as having this same topology: MCM-22, ERB-1, ITQ-1, PSH-3, and SSZ-25.

The MCM-22 family molecular sieves have been found to be useful in a variety of hydrocarbon conversion processes. Examples of MCM-22 family molecular sieve are MCM-22, MCM-49, MCM-56, ITQ-1, PSH-3, SSZ-25, and ERB-1. Such molecular sieves are useful for alkylation of aromatic compounds. For example, U.S. Pat. No. 6,936,744 discloses a process for producing a monoalkylated aromatic compound, particularly cumene, comprising the step of contacting a polyalkylated aromatic compound with an alkylatable aromatic compound under at least partial liquid phase conditions and in the presence of a transalkylation catalyst to produce the monoalkylated aromatic compound, wherein the transalkylation catalyst comprises a mixture of at least two different crystalline molecular sieves, wherein each of the molecular sieves is selected from zeolite beta, zeolite Y, mordenite and a material having an X-ray diffraction pattern including d-spacing maxima at 12.4±0.25, 6.9±0.15, 3.57±0.07 and 3.42±0.07 Angstroms.

It is known that crystal morphology, size and aggregation/agglomeriation can affect catalyst behavior, especially regarding catalyst activity and stability. There is, therefore, a need for novel crystalline molecular sieve compositions and method of making such novel crystalline molecular sieve compositions, especially molecular sieves of different morphology.

SUMMARY OF THIS DISCLOSURE

In some embodiments, this disclosure relates to a crystalline MCM-22 family molecular sieve having, in its as-synthesized form, a platelet aggregates morphology, preferably the platelet aggregates morphology is rosette habit morphology.

In some aspects of this disclosure, the platelike crystal of the molecular sieve is multiple layer plate. In additional aspects of this disclosure, the platelike crystal of the molecular sieve comprises multiple sub-crystals.

In some embodiments of this disclosure, greater than 50 wt % of the molecular sieve having a crystal diameter greater than 1 μm, preferably greater than 2 μm, optionally greater than 5 μm, as measured by the SEM.

In some aspects of this disclosure, greater than 50 wt % of the crystalline molecular sieve having a crystal thickness of about 0.04 μm as measured by the SEM.

In additional embodiments, this disclosure relates to a method of manufacturing the crystalline MCM-22 family molecular sieve, the method comprising the steps of:

(a) combining at least one silicon source, at least one source of at least one alkali or alkali earth metal element, at least one directing-agent (R), water, and optionally at least one aluminum source, to form a mixture having the following mole composition:

| | |
|---|---|
| $Si:Al_2 =$ | 10 to infinity |
| $H_2O:Si =$ | 1 to 10000 |
| $OH^-:Si =$ | 0.001 to 2 |
| $M^+:Si =$ | 0.001 to 2 |
| $R:Si =$ | 0.001 to 2 | wherein M is an alkali metal and R is selected from the group consisting of cyclopentylamine, cyclohexylamine, cycloheptylamine, hexamethyleneimine, heptamethyleneimine, homopiperazine, and combinations thereof;

(b) submitting the mixture at crystallization conditions to form a product comprising the desired crystalline molecular sieve, wherein the crystallization conditions comprise a temperature in the range of from 100° C. to 250° C., a crystallization time from about 1 hour to 200 hours; and optionally a stirring speed in the range of from 0 to less than about 60; and (c) recovering the molecular sieve.

Additionally, this disclosure relates to a process for hydrocarbon conversion, comprising the step of:

(a) contacting a hydrocarbon feedstock with the crystalline MCM-22 family molecular sieve of this disclosure, under conversion conditions to form a conversion product.

These and other facets of the present invention shall become apparent from the following detailed description, Figures, and appended claims.

DESCRIPTION OF THE FIGURES

FIG. 1 shows the X-ray diffraction patterns of the as-synthesized MCM-22 family molecular sieve products of Example A.

FIG. 2 shows the SEM image of the as-synthesized MCM-22 family molecular sieve product of Example A.

FIG. 3A shows the X-ray diffraction patterns of the as-synthesized MCM-22 family molecular sieve products of Example 1 at 120 hrs.

FIG. 3B shows the X-ray diffraction patterns of the as-synthesized MCM-22 family molecular sieve products of Example 1 at 168 hrs.

FIG. 4 shows the SEM image of the as-synthesized MCM-22 family molecular sieve product of Example 1.

FIG. 5 shows the X-ray diffraction patterns of the as-synthesized MCM-22 family molecular sieve products of Example 2.

FIG. 6A shows the SEM image of the as-synthesized MCM-22 family molecular sieve product of Example 2.

FIG. 6B shows the SEM image of the as-synthesized MCM-22 family molecular sieve product of Example 2.

FIG. 7 shows the X-ray diffraction patterns of the as-synthesized MCM-22 family molecular sieve products of Example 3 at 48 hrs.

FIG. 8 shows the SEM image of the as-synthesized MCM-22 family molecular sieve product of Example 3.

FIG. 9 shows the X-ray diffraction patterns of the as-synthesized MCM-22 family molecular sieve products of Example 4.

FIG. 10 shows the SEM image of the as-synthesized MCM-22 family molecular sieve product of Example 4.

DETAILED DESCRIPTION OF THIS DISCLOSURE

Introduction

All patents, patent applications, test procedures, priority documents, articles, publications, manuals, and other documents cited herein are fully incorporated by reference to the extent such disclosure is not inconsistent with the present invention and for all jurisdictions in which such incorporation is permitted.

When numerical lower limits and numerical upper limits are listed herein, ranges from any lower limit to any upper limit are contemplated.

As used in this specification, the term "framework type" is used in the sense described in the "Atlas of Zeolite Framework Types," 2001.

As used herein, the numbering scheme for the Periodic Table Groups is used as in Chemical and Engineering News, 63(5), 27 (1985).

The term "rosette habit" morphology as used herein means a platelet mineral composed "rosette stacked thin platelike crystals." Crystalline materials having rosette habit morphology are illustrated in FIG. 4 and FIG. 5 of the American Mineralogist, Vol. 66, pages 1054-1062, illustrate the photomicrographs of minerals with rosette morphology. The entirety of the American Mineralogist, Vol. 66, pages 1054-1062 is incorporated herein by reference. FIG. 6 of this disclosure shows the crystalline MCM-22 family molecular sieves of this disclosure with rosette morphology.

The term "platelet" morphology as used herein means a mineral composed "thin platelike crystals." These thin platelike crystals may aggregate together to form a material having platelet aggregates morphology. The platelike crystals may also compose of multiple layers. FIG. 2 of this disclosure shows the crystalline MCM-22 family molecular sieves with platelet morphology. FIGS. 4, 8, and 10 of this disclosure shows the crystalline MCM-22 family molecular sieves of this disclosure with platelet morphology and/or aggregate platelet morphology.

It will be understood by a person skilled in the art that the MCM-22 family material may contain impurities, such as amorphous materials; unit cells having non-MWW framework topologies (e.g., MFI, MTW); and/or other impurities (e.g., heavy metals and/or organic hydrocarbons). Typical examples of the non-MCM-22 family molecular sieve(s) co-existing with the MCM-22 family molecular sieve(s) of this disclosure are Kenyaite, EU-1, ZSM-50, ZSM-12, ZSM-48, ZSM-5, Ferrierite, Mordenite, Sodalite, and/or Analcine. Other examples of the non-MCM-22 family molecular sieve(s) co-existing with the MCM-22 family molecular sieve(s) of this disclosure are molecular sieves having framework type of EUO, MTW, FER, MOR, SOD, ANA, and/or MFI. The MCM-22 family materials of this disclosure are preferably substantially free of non-MCM-22 family material(s). The term "substantially free of non-MCM-22 family material(s)" used herein means the MCM-22 family material of this disclosure preferably contains a minor proportion (less than 50 wt %), preferably less than 20 wt %, of non-MCM-22 family materials ("impurities") in the MCM-22 family materials, which weight percent (wt %) values are based on the combined weight of impurities and pure phase MCM-22 family materials.

The MCM-22 crystalline material has a composition involving the molar relationship:

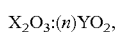

$$X_2O_3:(n)YO_2,$$

wherein X is a trivalent element, such as aluminum, boron, iron and/or gallium, preferably aluminum, Y is a tetravalent element such as silicon and/or germanium, preferably silicon, and n is at least about 10, usually from about 10 to about 150, more usually from about 10 to about 60, and even more usually from about 20 to about 40. In the as-synthesized form, the material typically has a formula, on an anhydrous basis and in terms of moles of oxides per n moles of $YO_2$, as follows:

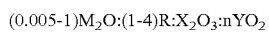

$$(0.005-1)M_2O:(1-4)R:X_2O_3:nYO_2$$

wherein M is an alkali or alkaline earth metal, and R is an organic moiety. The M and R components are associated with the material as a result of their presence during synthesis, and are typically removed by post-synthesis methods well known to those skilled in the art and/or hereinafter more particularly described.

It is to be understood that throughout this detailed description, common characterization techniques were used to describe molecular sieve materials. These common techniques included ascertaining:

(a) structure and the degree of crystallinity of the molecular sieve material by X-Ray Diffraction (XRD);

(b) morphology and crystal size of the molecular sieve material measured by Scanning Electron Microscope (SEM);

(c) chemical composition by atomic absorption spectrometry and/or Inductively Coupled Plasma Mass Spectrometry (ICP-MS or ICPMS);

(d) adsorption capacities and surface areas measured by Brunauer-Emmett-Teller (BET) method; and/or (e) catalytic activities and catalytic stabilities measured by probing reactions.

X-Ray Powder Diffraction Pattern of Known MCM-22

The MCM-22 crystalline materials may be distinguished from other crystalline materials by the X-ray diffraction pattern.

The interplanar spacings, d's, were calculated in Angstrom units (Å), and the relative intensities of the lines, $I/I_o$, where the intensity of the strongest line above background, $I_o$, is counted as 100, were derived with the use of a profile fitting routine (or second derivative algorithm). The intensities are uncorrected for Lorentz and polarization effects. The relative intensities are given in terms of the symbols VS=very strong (greater than 60 to 100), S=strong (greater than 40 to 60), M=medium (greater than 20 to 40) and W=weak (0 to 20). It should be understood that diffraction data listed as single lines may consist of multiple overlapping lines which under certain conditions, such as differences in crystallographic changes, may appear as resolved or partially resolved lines. Typically, crystallographic changes can include minor changes in unit cell parameters and/or a change in crystal symmetry, without a change in the structure. These minor effects, including changes in relative intensities, can also occur as a result of differences in cation content, framework composition, nature and degree of pore filling, and thermal and/or hydrothermal history. Other changes in diffraction patterns can be indicative of important differences between materials, which is the case for comparing MCM-22 with similar materials, e.g., MCM-49, MCM-56, and PSH-3.

It should be understood that this X-ray diffraction pattern is characteristic of all the species of the present crystalline composition. The sodium form as well as other cationic forms reveal substantially the same pattern with some minor shifts in interplanar spacing and variation in relative intensity. Other minor variations can occur, depending on the Y to X, e.g., silicon to aluminum, ratio of the particular sample, as well as its degree of thermal treatment (e.g., calcination).

In its as-synthesized form, the known MCM-22 crystalline material has an X-ray diffraction pattern which is distinguished from the patterns of other known crystalline materials by the lines listed in Table I below:

TABLE I

| Interplanar d-Spacing (Å) | Relative Intensity, $I/I_0 \times 100$ |
|---|---|
| 13.53 ± 0.20 | M-VS |
| 12.38 ± 0.20 | M-VS |
| 11.13 ± 0.20 | W-S |
| 9.15 ± 0.15 | W-S |
| 6.89 ± 0.15 | W-M |
| 4.47 ± 0.10 | W-M |
| 3.95 ± 0.08 | W-VS |
| 3.56 ± 0.06 | W-M |
| 3.43 ± 0.06 | M-VS |
| 3.36 ± 0.05 | W-S |

A particular example of such an as-synthesized material is the material of Example 1 of the aforementioned U.S. Pat. No. 4,954,325. This material of Example 1 of U.S. Pat. No. 4,954,325 has the X-ray diffraction pattern given in the following Table II:

TABLE II

| 2 Theta | Interplanar d-Spacing (Å) | Relative Intensity, $I/I_0 \times 100$ |
|---|---|---|
| 3.1 | 28.5 | 14 |
| 3.9 | 22.7 | <1 |
| 6.53 | 13.53 | 36 |
| 7.14 | 12.38 | 100 |
| 7.94 | 11.13 | 34 |
| 9.67 | 9.15 | 20 |
| 12.85 | 6.89 | 6 |
| 13.26 | 6.68 | 4 |
| 14.36 | 6.17 | 2 |
| 14.70 | 6.03 | 5 |
| 15.85 | 5.59 | 4 |
| 19.00 | 4.67 | 2 |
| 19.85 | 4.47 | 22 |
| 21.56 | 4.12 | 10 |
| 21.94 | 4.05 | 19 |
| 22.53 | 3.95 | 21 |
| 23.59 | 3.77 | 13 |
| 24.98 | 3.56 | 20 |
| 25.98 | 3.43 | 55 |
| 26.56 | 3.36 | 23 |
| 29.15 | 3.06 | 4 |
| 31.58 | 2.833 | 3 |
| 32.34 | 2.768 | 2 |
| 33.48 | 2.676 | 5 |
| 34.87 | 2.573 | 1 |
| 36.34 | 2.472 | 2 |
| 37.18 | 2.418 | 1 |
| 37.82 | 2.379 | 5 |

Scanning Electron Microscope (SEM)

The SEM image of an MCM-22 molecular sieve produced according to the method of manufacturing of U.S. Pat. No. 4,954,325 is shown in FIG. 2. The MCM-22 molecular sieve according to method of manufacturing of U.S. Pat. No. 4,954,325 has a thin layered less defined hexagonal platelets morphology and an average platelet diameter of less than about 1 µm, determined by the SEM (FIG. 2). The majority of the platelet crystal has an average platelet diameter of less than about 0.5 micron (µm).

The SEM images of the crystalline MCM-22 family molecular sieve of this disclosure are shown in FIGS. 4, 6, 8, and 10. A majority, preferably greater than 51 wt %, more preferably greater than 75 wt %, of the crystals of the crystalline MCM-22 molecular sieves, has an average platelet diameter greater than 1 µm, preferably greater than 2 µm, more preferably greater than 3 µm, in some instances greater than 5 µm. In addition, a majority, preferably greater than 51 wt %, more preferably greater than 75 wt %, of the crystals of the crystalline MCM-22 molecular sieves, has an average platelet thickness of about 0.04 to about 0.05 µm.

The SEM images of crystalline molecular sieves (after calcination) of this disclosure (FIGS. 4, 6, 8, and 10) have a platelet aggregates morphology, wherein platelike crystals are composed of multiple layers or multiple platelike sub-crystals. The crystalline MCM-22 family molecular sieve (after calcination) of this disclosure (FIG. 6) further shows a rosette habit morphology.

Surface Areas and Adsorption Uptake

The overall surface area of a molecular sieve may be measured by the Brunauer-Emmett-Teller (BET) method using adsorption-desorption of nitrogen (temperature of liquid nitrogen, 77 K). The internal surface area may be calculated using t-plot of the Brunauer-Emmett-Teller (BET) measurement. The external surface area is calculated by subtracting the internal surface area from the overall surface area measured by the Brunauer-Emmett-Teller (BET) measurement.

The crystalline molecular sieve (after calcination) of this disclosure may be characterized by a preferred total surface area (sum of the external and the internal surface areas, as measured by the BET method) of greater than 450 m$^2$/g, more preferably greater than 475 m 2/g, more preferably greater than 500 m 2/g, and more preferably greater than 600 m$^2$/g.

Formulation of the Hydrothermal Reaction Mixtures

Synthetic molecular sieves are often prepared from aqueous hydrothermal reaction mixtures (synthesis mixture(s) or synthetic gel(s)) comprising sources of appropriate oxides. Organic directing agents may also be included in the hydrothermal reaction mixture for the purpose of influencing the production of a molecular sieve having the desired structure. The use of such directing agents is discussed in an article by Lok et al. entitled "The Role of Organic Molecules in Molecular Sieve Synthesis" appearing in Zeolites, Vol. 3, October, 1983, pp. 282-291.

After the components of the hydrothermal reaction mixture are properly mixed with one another, the hydrothermal reaction mixture is subjected to appropriate crystallization conditions. Such conditions usually involve heating of the hydrothermal reaction mixture to an elevated temperature possibly with stirring. Room temperature aging of the hydrothermal reaction mixture is also desirable in some instances.

After the crystallization of the hydrothermal reaction mixture is complete, the crystalline product may be recovered from the remainder of the hydrothermal reaction mixture, especially the liquid contents thereof. Such recovery may involve filtering the crystals and washing these crystals with water. However, in order to remove the entire undesired residue of the hydrothermal reaction mixture from the crystals, it is often necessary to subject the crystals to a high temperature calcination e.g., at 500° C., possibly in the presence of oxygen. Such a calcination treatment not only removes water from the crystals, but this treatment also serves to decompose and/or oxidize the residue of the organic directing agent which may be occluded in the pores of the crystals, possibly occupying ion exchange sites therein.

The crystalline molecular sieve material of this disclosure may be prepared from a hydrothermal reaction mixture containing sources of alkali or alkaline earth metal (M), e.g., sodium, or potassium, cation, an oxide of trivalent element X, e.g., aluminum, an oxide of tetravalent element Y, e.g., silicon, an organic (R) directing agent, hereinafter more particularly described, and water, the hydrothermal reaction mixture having a composition, in terms of mole ratios of oxides, within the following ranges:

TABLE XI

| Reactants | Useful | Preferred |
|---|---|---|
| $YO_2/X_2O_3$ | 10 to infinity | 15-55 |
| $H_2O/YO_2$ | 1 to 10000 | 5-40 |
| $OH^-/YO_2$* | 0.001-2 | 0.1-1 |
| $M/YO_2$ | 0.001-2 | 0.1-1 |
| $R/YO_2$ | 0.001-2 | 0.01-0.5 |
| Seed** | 0-25 wt % | 1-5 wt % |
| R | HMI | HMI |

*The $OH^-/YO_2$ is calculated without correction of trivalent element source.
**The weight percent (wt %) of seed is based on the weight of the solid tetrahedral element oxide.

The sources of the various elements required in the final product may be any of those in commercial use or described in the literature, as may the method of preparation of the synthesis mixture.

Y is a tetravalent element selected from Groups 4-14 of the Periodic Table of the Elements, such as silicon and/or germanium, preferably silicon. In some embodiments of this disclosure, the source of $YO_2$ comprises solid $YO_2$, preferably about 30 wt % solid $YO_2$ in order to obtain the crystal product of this disclosure. When $YO_2$ is silica, the use of a silica source containing preferably about 30 wt % solid silica, e.g., silica sold by Degussa under the trade names Aerosil or Ultrasil (a precipitated, spray dried silica containing about 90 wt % silica), an aqueous colloidal suspension of silica, for example one sold by Grace Davison under the trade name Ludox, or HiSil (a precipitated hydrated $SiO_2$ containing about 87 wt % silica, about 6 wt % free $H_2O$ and about 4.5 wt % bound $H_2O$ of hydration and having a particle size of about 0.02 micron) favors crystal formation from the above mixture. Preferably, therefore, the $YO_2$, e.g., silica, source contains about 30 wt % solid $YO_2$, e.g., silica, and more preferably about 40 wt % solid $YO_2$, e.g., silica. The source of silicon may also be a silicate, e.g., an alkali metal silicate, or a tetraalkyl orthosilicate.

In additional embodiments of this disclosure, the source of $YO_2$ comprises acid of the tetravalent element (Y). When $YO_2$ is silica, the silica source may be silicic acid.

X is a trivalent element selected from Groups 3-13 of the Periodic Table of the Elements, such as aluminum, and/or boron, and/or iron and/or gallium, preferably aluminum. The source of $X_2O_3$, e.g., aluminum, is preferably aluminum sulphate or hydrated alumina. Other aluminum sources include, for example, other water-soluble aluminum salts, sodium aluminate, or an alkoxide, e.g., aluminum isopropoxide, or aluminum metal, e.g., in the form of chips.

The alkali or alkali earth metal element is advantageously lithium, sodium, potassium, calcium, or magnesium. The source of alkali or alkali earth metal element is advantageously being metal oxide, metal chloride, metal fluoride, metal sulfate, metal nitrate, or metal aluminate. The sodium source advantageously being sodium hydroxide or sodium aluminate. The alkali metal may also be replaced by ammonium ($NH_4^+$) or its equivalents, e.g., alkyl-ammonium ion.

In some embodiments of this disclosure, the $M:YO_2$, e.g., $M:SiO_2$ molar ratio ranges from a low value of 0.001, preferably 0.01, and optionally 0.1, to a high value of 2.0, preferably 1, and optionally 0.5. The $M:YO_2$, e.g., $M:SiO_2$ molar ratio ideally falls in a range comprising any combination of the above-mentioned low value(s) and the above-mentioned high values(s).

In some embodiments of this disclosure, the $H_2O:YO_2$, e.g., $H_2O:SiO_2$ molar ratio ranges from a low value of 1, preferably 5, and optionally 10, to a high value of 10000, preferably 5000, and optionally 500. The $H_2O:YO_2$, e.g., $H_2O:SiO_2$ molar ratio ideally falls in a range comprising any combination of the above-mentioned low value(s) and the above-mentioned high values(s).

The $OH^-:YO_2$, e.g., $OH^-:SiO_2$ molar ratio as used in this disclosure does not include correction of acid in the hydrothermal reaction mixture. It is calculated based on the total mole of hydroxide added to the hydrothermal reaction mixture. The hydroxide ($OH^-$) source is advantageously alkali metal oxide, e.g., $Li_2O$, $Na_2O$, $K_2O$, $Rb_2O$, $Cs_2O$, $Fr_2O$, or any combination thereof; alkali metal hydroxide, e.g., LiOH, NaOH, KOH, RbOH, CsOH, FrOH, or any combination thereof; ammonium hydroxide, alkali earth metal oxide, e.g., BeO, MgO, CaO, SrO, BaO, RaO, or any combination thereof; alkali earth metal hydroxide, e.g., $Be(OH)_2$, $Mg(OH)_2$, $Ca(OH)_2$, $Sr(OH)_2$, $Ba(OH)_2$, $Ra(OH)_2$, or any combination thereof; oxide(s) or hydroxide(s) of any element selected from Groups 3-17; and any combination thereof.

In some embodiments of this disclosure, the OH—:$YO_2$, e.g., OH—:$SiO_2$ molar ratio ranges from a low value of 0.001, preferably 0.01, and optionally 0.1, to a high value of 2.0, preferable 1, and optionally 0.5. The $OH^-:YO_2$, e.g., $OH^-:SiO_2$ molar ratio ideally falls in a range comprising any combination of the above-mentioned low value(s) and the above-mentioned high values(s).

Directing agent R is selected from the group consisting of cycloalkylamine, azacycloalkane, diazacycloalkane, and mixtures thereof, alkyl comprising from 5 to 8 carbon atoms. Non-limiting examples of R include cyclopentylamine, cyclohexylamine, cycloheptylamine, hexamethyleneimine, heptamethyleneimine, homopiperazine, and combinations thereof.

A factor affecting the cost and the product quality of the synthesis of a crystalline molecular sieve is the amount of the directing agent (represented by the $R:YO_2$, e.g., $R:SiO_2$ molar ratio). The directing agent is generally the most expensive reactant(s) in the hydrothermal reaction mixture of many crystalline molecular sieves. The lower the amount of the directing agent in the hydrothermal reaction mixture (low $R:YO_2$, e.g., $R:SiO_2$ molar ratio), the cheaper the final molecular sieve produced.

In some embodiments of this disclosure, the $R:YO_2$, e.g., $R:SiO_2$ molar ratio ranges from a low value of 0.001, preferably 0.05, and optionally 0.1, to a high value of 2, preferably 0.5, more preferably 0.4. The $R:YO_2$, e.g., $R:SiO_2$ molar ratio ideally falls in a ranges comprising any combination of the above-mentioned low value(s) and the above-mentioned high values(s).

It should be realized that the hydrothermal reaction mixture components can be supplied by more than one source. The hydrothermal reaction mixture can be prepared either batchwise or continuously. Crystal size and crystallization time of the crystalline molecular sieve of this disclosure may vary with the nature of the hydrothermal reaction mixture employed and the crystallization conditions.

It will be understood by a person skilled in the art that the synthesis mixture having a composition within the molar ranges as discussed above means that the synthesis mixture is the product of mixing, adding, reacting, or by any means of providing such a mixture, wherein such product has a composition within the molar ranges as discussed above. The product of mixing, adding, reacting, or by any means of providing such a mixture may or may not contain individual ingredients when the synthesis mixture was prepared. The product of mixing, adding, reacting, or by any means of providing such a mixture, may even contain reaction product of individual ingredients when the synthesis mixture was prepared by mixing, adding, reacting, or by any means of providing such a mixture.

Optionally the hydrothermal reaction mixture may contain seed crystals. It is well known that seeding a molecular sieve synthesis mixture frequently has beneficial effects, for example in controlling the particle size of the product, avoiding the need for an organic template, accelerating synthesis, and improving the proportion of product that is of the intended framework type. In some embodiments of this disclosure, the synthesis of the crystalline molecular sieve is facilitated by the presence of 0 to about 25 wt %, preferably about 1 to about 5 wt %, seed crystals based on total weight of tetrahedral element oxide (e.g., silica) of the hydrothermal reaction mixture.

Usually the seeding crystals are from the synthesis similar to the one where they are used. In general any form of the crystalline material may be useful in facilitating synthesis on the new phase.

Crystallization Conditions

Crystallization of the crystalline molecular sieve of this disclosure can be carried out at either static or stirred condition in a reactor vessel, such as for example, autoclaves. The total useful range of temperatures for crystallization is from about 100° C. to about 250° C. for a time sufficient for crystallization to occur at the temperature used, e.g., from about 1 hour to about 400 hours. Preferably, the range of temperatures for crystallization is from about 140° C. to about 180° C. for a time sufficient for crystallization to occur at the temperature used, e.g., from about 1 hour to about 200 hours.

The hydrothermal reaction of this disclosure is carried out without agitation (static) or with any type of agitation, e.g., stirring or rotating the vessel about a horizontal axis (tumbling). The rate of the agitation is ranged from 0 to less than about 60 RPM, preferably from 0 to less than 35 RPM.

Thereafter, the crystals are separated from the liquid and recovered. The procedure may include an aging period, either at room temperature (~25° C.) or, preferably, at a moderately elevated temperature, before the hydrothermal treatment ("hydrothermal reaction") at more elevated temperature. The latter may include a period of gradual or stepwise variation in temperature.

In some embodiments, the crystalline MCM-22 family molecular sieve of this disclosure comprises at least one of MCM-22, MCM-49, MCM-56, an intergrowth-phase of MCM-22, and/or MCM-49, and/or MCM-56, or a mix phase of MCM-22, and/or MCM-49, and/or MCM-56.

The molecular sieve product from the synthesis may further be filtrated, washed with water, and/or dried. The crystalline molecular sieve formed by crystallization may be recovered and subjected for further treatment, such as, ion-exchange with ammonium salt(s) (e.g., ammonium hydroxide, ammonium nitrate, ammonium chloride, ammonium sulfate, ammonium phosphate, or any combination thereof) and/or calcination in an oxidative atmosphere (e.g., air, gas with an oxygen partial pressure of greater than 0 kpa-a) at a temperature of greater than 200° C., preferably at least 300° C., more preferably at least 400° C., and most preferably at least 500° C.

Catalysis and Adsorption

A summary of the molecular sieves and/or zeolites, in terms of production, modification and characterization of molecular sieves, is described in the book "Molecular Sieves—Principles of Synthesis and Identification"; (R. Szostak, Blackie Academic & Professional, London, 1998, Second Edition). In addition to molecular sieves, amorphous materials, chiefly silica, aluminum silicate and aluminum oxide, have been used as adsorbents and catalyst supports. A number of long-known forming techniques, like spray drying, prilling, pelletizing and extrusion, have been and are being used to produce macrostructures in the form of, for example, spherical particles, extrudates, pellets and Tablets of both micropores and other types of porous materials for use in catalysis, adsorption and ion exchange. A summary of these techniques is described in "Catalyst Manufacture," A. B. Stiles and T. A. Koch, Marcel Dekker, New York, 1995.

To the extent desired, the original metal cations of the as-synthesized material can be replaced in accordance with techniques well known in the art, at least in part, by ion exchange with other cations. Preferred replacing cations include metal ions, hydrogen ions, hydrogen precursor, e.g., ammonium, ions and mixtures thereof. Particularly preferred cations are those which tailor the catalytic activity for certain hydrocarbon conversion reactions. These include hydrogen, rare earth metals and metals of Groups 1-17, preferably Groups 2-12 of the Periodic Table of the Elements.

The crystalline molecular sieve of this disclosure, preferably the MCM-22 family molecular sieve, when employed either as an adsorbent or as a catalyst in an organic compound conversion process should be generally dehydrated, at least partially. This can be done by heating to a temperature in the range of e.g., 200° C. to 595° C. in an atmosphere such as air or nitrogen, and at atmospheric, sub-atmospheric or super-atmospheric pressures for e.g., between 30 minutes and 48 hours. The degree of dehydration is measured by the percentage of weight loss relative to the total weight loss of a molecular sieve sample at 595° C. under flowing dry nitrogen (less than 0.001 kPa partial pressure of water vapor) for 48 hours. Dehydration can also be performed at room temperature (~25° C.) merely by placing the silicate in a vacuum, but a longer time is required to obtain a sufficient amount of dehydration.

When used as a catalyst, the crystalline molecular sieve of this disclosure, preferably the MCM-22 family molecular sieve, should be generally subjected to thermal treatment to remove part or all of any organic constituent. The crystalline molecular sieve of this disclosure, preferably the MCM-22 family molecular sieve, can also be used as a catalyst in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such component can be in the composition by way of co-crystallization, exchanged into the composition to the extent a Group 13 element, e.g., aluminum, is in the structure, impregnated therein or intimately physically admixed therewith. Such component can be impregnated in or on to it such as, for example, by, in the case of platinum, treating the silicate with a solution containing a platinum metal-containing ion. Thus, suitable platinum compounds for this purpose include chloroplatinic acid, platinous chloride and various compounds containing the platinum amine complex.

The crystalline MCM-22 family molecular sieve of this disclosure, especially in its metal, hydrogen and ammonium forms can be beneficially converted to another form by thermal treatment. This thermal treatment is generally performed by heating one of these forms at a temperature of at least 370° C. for at least 1 minute and generally not longer than 1000 hours. While sub-atmospheric pressure can be employed for the thermal treatment, atmospheric pressure is desired for reasons of convenience. The thermal treatment can be performed at a temperature up to about 925° C. The thermal treated product is particularly useful in the catalysis of certain hydrocarbon conversion reactions. The thermally treated product, especially in its metal, hydrogen and ammonium forms, is particularly useful in the catalysis of certain organic, e.g., hydrocarbon, conversion reactions. Non-limiting examples of such reactions include those described in U.S. Pat. Nos. 4,954,325; 4,973,784; 4,992,611; 4,956,514; 4,962,250; 4,982,033; 4,962,257; 4,962,256; 4,992,606; 4,954,663; 4,992,615; 4,983,276; 4,982,040; 4,962,239; 4,968,402; 5,000,839; 5,001,296; 4,986,894; 5,001,295; 5,001,283; 5,012,033; 5,019,670; 5,019,665; 5,019,664; and 5,013,422, each incorporated herein by reference as to the description of the catalytic reactions.

The crystals prepared by the instant invention can be shaped into a wide variety of particle sizes. Generally speaking, the particles can be in the form of a powder, a granule, or a molded product, such as an extrudate. In cases where the catalyst is molded, such as by extrusion, the crystals can be extruded before drying or partially dried and then extruded.

The crystalline MCM-22 family molecular sieve of this disclosure may be used as an adsorbent, such as for separating at least one component from a mixture of components in the vapor or liquid phase having differential sorption characteristics with respect to the crystalline molecular sieve(s) of this disclosure. Therefore, at least one component can be partially or substantially totally separated from a mixture of components having differential sorption characteristics with respect to the crystalline molecular sieve(s) of this disclosure by contacting the mixture with the crystalline molecular sieve(s) of this disclosure to selectively sorb the one component.

The crystalline MCM-22 family molecular sieve(s) of this disclosure, are useful as catalyst in a wide range of processes, including separation processes and hydrocarbon conversion processes. Specific examples of hydrocarbon conversion processes which are effectively catalyzed by the crystalline MCM-22 family molecular sieve(s) of this disclosure, by itself or in combination with one or more other catalytically active substances including other crystalline catalysts, include the following:

(i) alkylation of aromatic hydrocarbons, e.g., benzene, with long chain olefins, e.g., $C_{14}$ olefin, with reaction conditions including, individually or in any combination, a temperature of from about 340° C. to about 500° C., a pressure of from about 101 to about 20200 kPa-a (absolute), a weight hourly space velocity of from about 2 $hr^{-1}$ to about 2000 $hr^{-1}$ and an aromatic hydrocarbon/olefin mole ratio of from about 1/1 to about 20/1, to provide long chain alkyl aromatics which can be subsequently sulfonated to provide synthetic detergents;

(ii) alkylation of aromatic hydrocarbons with gaseous olefins to provide short chain alkyl aromatic compounds, e.g., the alkylation of benzene with propylene to provide cumene, with reaction conditions including, individually or in any combination, a temperature of from about 10° C. to about 125° C., a pressure of from about 101 to about 3030 kPa-a, and an aromatic hydrocarbon weight hourly space velocity (WHSV) of from 5 $hr^{-1}$ to about 50 $hr^{-1}$;

(iii) alkylation of reformate containing substantial quantities of benzene and toluene with fuel gas containing $C_5$ olefins to provide, inter alia, mono- and di-alkylates with reaction conditions including, individually or in any combination, a temperature of from about 315° C. to about 455° C., a pressure of from about 3000 to about 6000 kPa-a, a WHSV-olefin of from about 0.4 $hr^{-1}$ to about 0.8 $hr^{-1}$, a WHSV-reformate of from about 1 $hr^{-1}$ to about 2 $hr^{-1}$ and a gas recycle of from about 1.5 to 2.5 vol/vol fuel gas feed;

(iv) alkylation of aromatic hydrocarbons, e.g., benzene, toluene, xylene and naphthalene, with long chain olefins, e.g., $Cl_4$ olefin, to provide alkylated aromatic lube base stocks with reaction conditions including, individually or in any combination, a temperature of from about 160° C. to about 260° C. and a pressure of from about 2600 to 3500 kPa-a;

(v) alkylation of phenols with olefins or equivalent alcohols to provide long chain alkyl phenols with reaction conditions including, individually or in any combination, a temperature of from about 200° C. to about 250° C., a pressure of from about 1500 to 2300 kPa-a and a total WHSV of from about 2 $hr^{-1}$ to about 10 $hr^{-1}$;

(vi) conversion of light paraffins to olefins and aromatics with reaction conditions including, individually or in any combination, a temperature of from about 425° C. to about 760° C. and a pressure of from about 170 to about 15000 kPa-a;

(vii) conversion of light olefins to gasoline, distillate and lube range hydrocarbons with reaction conditions including, individually or in any combination, a temperature of from about 175° C. to about 375° C. and a pressure of from about 800 to about 15000 kPa-a;

(viii) two-stage hydrocracking for upgrading hydrocarbon streams having initial boiling points above about 260° C. to premium distillate and gasoline boiling range products in a first stage using the MCM-22 family molecular sieve of this disclosure in combination with a Groups 8-10 metal as catalyst with effluent therefrom being reaction in a second stage using zeolite Beta, also in combination with a Groups 8-10 metal, as catalyst, the reaction conditions including, individually or in any combination, a temperature of from about 340° C. to about 455° C., a pressure of from about 3000 to about 18000 kPa-a, a hydrogen circulation of from about 176 to about 1760 liter/liter and a liquid hourly space velocity (LHSV) of from about 0.1 to 10 $h^{-1}$;

(ix) a combination hydrocracking/dewaxing process in the presence of the MCM-22 family molecular sieve of this disclosure and a hydrogenation component as catalyst, or a mixture of such catalyst and zeolite Beta, with reaction conditions including, individually or in any combination, a temperature of from about 350° C. to about 400° C., a pressure of from about 10000 to about 11000 kPa-a, an LHSV of from about 0.4 to about 0.6 and a hydrogen circulation of from about 528 to about 880 liter/liter;

(x) reaction of alcohols with olefins to provide mixed ethers, e.g., the reaction of methanol with isobutene and/or isopentene to provide methyl-t-butyl ether (MTBE) and/or t-amyl methyl ether (TAM) with conversion conditions including, individually or in any combination, a temperature of from about 20° C. to about 200° C., a pressure of from 200 to about 20000 kPa-a, a WHSV (gram-olefin per hour gram-zeolite) of from about 0.1 hr$^{-1}$ to about 200 hr$^{-1}$ and an alcohol to olefin molar feed ratio of from about 0.1/1 to about 5/1;

(xi) toluene disproportionation with $C_9^+$ aromatics as co-feed with reaction conditions including, individually or in any combination, a temperature of from about 315° C. to about 595° C., a pressure of from about 101 to about 7200 kPa-a, a hydrogen/hydrocarbon mole ratio of from about 0 (no added hydrogen) to about 10 and a WHSV of from about 0.1 hr$^{-1}$ to about 30 hr$^{-1}$;

(xii) preparation of the pharmaceutically-active compound 2-(4-isobutylphenyl) propionic acid, i.e. ibuprofen, by reacting isobutyl benzene with propylene oxide to provide the intermediate 2-(4-isobutylphenyl) propanol followed by oxidation of the alcohol to the corresponding carboxylic acid;

(xiii) use as an acid-binding agent in the reaction of amines with heterocyclic fiber-reactive components in preparation of dyes to prepare practically salt-free reactive dye-containing solution, as in German Patent No. DE 3,625,693, incorporated entirely herein by reference;

(xiv) as the absorbent for separating 2,6-toluene diisocyanate (2,6-TDI) from isomers if TDI as in U.S. Pat. No. 4,721,807, incorporated entirely herein by reference, whereby a feed mixture comprising 2,6-TDI and 2,4-TDI is contacted with the present MCM-22 family molecular sieve which has been cation-exchanged with K ions to absorb the 2,6-TDI, followed by recovering the 2,6-TDI by desorption with desorbent material comprising toluene;

(xv) as the absorbent for separating 2,4-TDI from its isomers as in U.S. Pat. No. 4,721,806, incorporated entirely herein by reference, whereby a feed mixture comprising 2,4-TDI and 2,6-TDI is contact with the present MCM-22 family molecular sieve which has been cation-exchanged with Na, Ca Li and/or Mg ions to absorb the 2,4-TDI, followed by recovering the 2,4-TDI by desorption with desorbent material comprising toluene; and (xvi) in a process for decreasing the durene content of a 90-200° C.+ bottoms fraction obtained from the catalytic conversion of methanol to gasoline which comprises contacting the durene-containing bottoms fraction with hydrogen over a catalyst of the present MCM-22 family molecular sieve with a hydrogenation metal, at conditions including, individually or in any combination, a temperature of from about 230° C. to about 425° C. and a pressure of from about 457 to about 22000 kPa-a.

In an embodiment, the crystalline MCM-22 family molecular sieve(s) of this disclosure may be used in processes that co-produce phenol and ketones that proceed through benzene alkylation, followed by formation of the alkylbenzene hydroperoxide and cleavage of the alkylbenzene hydroperoxide into phenol and ketone. In such processes, the crystalline MCM-22 family molecular sieve(s) of this disclosure are used in the first step, that is, benzene alkylation. Examples of such processes includes processes in which benzene and propylene are converted to phenol and acetone, benzene and $C_4$ olefins are converted to phenol and methyl ethyl ketone, such as those described for example in international application PCT/EP2005/008557, benzene, propylene and $C_4$ olefins are converted to phenol, acetone and methyl ethyl ketone, which, in this case can be followed by conversion of phenol and acetone to bis-phenol-A as described in international application PCT/EP2005/008554, benzene is converted to phenol and cyclohexanone, or benzene and ethylene are converted to phenol and methyl ethyl ketone, as described for example in PCT/EP2005/008551.

The crystalline MCM-22 family molecular sieve(s) of this disclosure, are useful in benzene alkylation reactions where selectivity to the monoalkylbenzene is required. Furthermore, the crystalline MCM-22 family molecular sieve(s) of this disclosure is particularly useful to produce selectively sec-butylbenzene from benzene and $C_4$ olefin feeds that are rich in linear butenes, as described in international application PCT/EP2005/008557. Preferably, this conversion is carried out by co-feeding benzene and the $C_4$ olefin feed with the catalyst of the present invention, at a temperature of about 60° C. to about 260° C., for example of about 100° C. to 200° C., a pressure of 7000 kPa-a or less, and a feed weight hourly space velocity (WHSV) based on $C_4$ alkylating agent of from about 0.1 to 50 h$^{-1}$, and a molar ratio of benzene to $C_4$ alkylating agent from about 1 to about 50.

The crystalline MCM-22 family molecular sieve(s) of this disclosure are also useful catalyst for transalkylations, such as, for example, polyalkylbenzene transalkylations.

In the case of many catalysts, it is desired to incorporate the new crystal with another material resistant to the temperatures and other conditions employed in organic conversion processes. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with the new crystal, i.e. combined therewith or present during synthesis of the new crystal, which is active, tends to change the conversion and/or selectivity of the catalyst in certain organic conversion processes. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. The materials, i.e. clays, oxides, etc., function as binders for the catalyst. It is desirable to provide a catalyst having good crush strength because in commercial use it is desirable to prevent the catalyst from breaking down into powder-like materials. These clay binders have been employed normally only for the purpose of improving the crush strength of the catalyst.

Naturally occurring clays which can be composited with the new crystal include the montmorillonite and kaolin family, which families include the subbentonites, and the kaolins commonly known as Dixie, McNamee, Georgia and Florida clays or others in which the main mineral constituent is halloysite, kaolinite, dictite, narcite, or anauxite. Such clays can be used in the raw state as originally mined or initially subjected to calcination, acid treatment or chemical modification. Binders useful for compositing with the present crystal also include inorganic oxides, notably alumina.

In addition to the foregoing materials, the new crystal can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of finely divided crystalline molecular sieve and inorganic oxide matrix vary widely, with the crystal content ranging from about 1 to about 99 percent by weight and more usually, particularly when the composite is prepared in the form of beads, in the range of about 20 to about 80 wt % of the composite.

These and other facets of the present invention is exemplified by the Following Examples.

EXAMPLES

In the Examples, the XRD diffraction patterns of the as-synthesized materials were recorded on a Bruker D4 X-Ray Powder Diffractometer using copper Kα radiation in the 2θ range of 2 to 40 degrees.

The SEM images were obtained on a HITACHI S4800 Field Emission Scanning Electron Microscope (SEM). The crystal size was measured by averaging the size of multiple crystals as shown in the SEM.

The crystallinity is defined as the ratio of the sum of the two main peaks, 7.1 and 26 (2θ), to the ratio of the sum of the same peaks in the standard (reference Example), multiplied by 100.

The BET surface area was measured by Micromeritics TriStar 3000 V6.05A (Micromeritics Corporation, Norcross, Ga.) using standard procedures with heat pretreatment at 350° C.

The external surface area over overall BET surface area ratio was calculated from the t-plot generated as part of the BET determination by nitrogen sorption.

The following Examples illustrate exemplary preferred embodiments:

Example A

In this example, MCM-22 was prepared according to the method of U.S. Pat. No. 4,954,325.

A hydrothermal reaction mixture was prepared from water, hexamethyleneimine (HMI) (Sigma-Aldrich Company), silica (Ultrasil™, Degussa Corp.), 45 wt % sodium aluminate solution (25.5% $Al_2O_3$, 19.5% $Na_2O$; USALCO), and 50 wt % sodium hydroxide solution. The mixture had the following molar composition as shown in Table XII:

TABLE XII

| | Example A |
|---|---|
| Molar composition | |
| $SiO_2/Al_2O_3$ | 30 |
| $H_2O/SiO_2$ | 19.8 |
| $OH^-/SiO_2$ | 0.17 |
| $Na^+/SiO_2$ | 0.17 |
| $HMI/SiO_2$ | 0.35 |
| Crystallization conditions | |
| Temperature (° C.) | 150 |
| Stirring speed (RPM) | 250 |
| Time (hr) | 72 |
| XRD Result | Pure Phase MCM-22 |
| Crystallinity (%) | 100 |
| $SiO_2/Al_2O_3$ (molar ratio) | 23 |
| Total Surface Area (m²/g) | 653 |
| Micropore Surface Area (m²/g) | 530 |
| External Surface Area (m²/g) | 123 |
| Mesitylene uptake (mg/g) | 29.8 |
| Mesitylene sorption rate (mg/g/min) | 68 |

The mixture was crystallized at 150° C. in an autoclave with stirring at 250 rotation per minute (RPM) for 72 hours. After crystallization, the hydrothermal reaction mixture slurry was filtered, washed with deionized (DI) water and dried at 120° C. The as-synthesized material had an XRD patterns (FIG. 1) substantially as shown in Table I and Table II. The resulting MCM-22 crystals had a $SiO_2/Al_2O_3$ molar ratio of ~23/1. The calcined MCM-22 crystals had a surface area of 653 m²/g (micropore surface area of 530 and external surface area of 123 m²/g). The SEM image (FIG. 2) of the as-synthesized product crystal showed a platelet morphology with an average crystal thickness of about 200 to about 300 Å. The estimate average platelet diameter was less than about 1 μm. The calcined material had a mesitylene uptake of about 29.8 mg/g and a mesitylene sorption rate of about 68 mg/g/min. After calcination, the material exhibited an XRD according to that reported in U.S. Pat. No. 4,954,325.

Examples 1-2

Two hydrothermal reaction mixture was prepared from water, hexamethyleneimine (HMI) (Sigma-Aldrich Company), silicic acid (Sigma-Aldrich Company), 45 wt. % sodium aluminate solution, and 50 wt. % sodium hydroxide solution. The mixtures had the following molar compositions as shown in the following Table XIII:

TABLE XIII

| | Example 1 | Example 2 |
|---|---|---|
| Molar composition | | |
| $SiO_2/Al_2O_3$ | 30 | 30 |
| $H_2O/SiO_2$ | 19.5 | 19.5 |
| $OH^-/SiO_2$ | 0.18 | 0.18 |
| $Na^+/SiO_2$ | 0.18 | 0.18 |
| $R/SiO_2$ | 0.35 | 0.35 |
| Crystallization conditions | | |
| Temperature (° C.) | 149 | 149 |
| Stirring speed (RPM) | 30 | 0 |
| Time (hr) | 168 | 216 |
| Characterizations | | |
| XRD Result | See FIG. 3 | See FIG. 5 |
| $SiO_2/Al_2O_3$ (molar ratio) | 23.2 | 23.2 |
| BET area (m²/g) | 629 | Not measured |
| Crystal size (SEM) | >1 μm × 0.025 μm | >1 μm wide |
| Morphology (SEM) | (FIG. 4) | (FIG. 6) |

The above mixtures were well mixed under vigorous stirring for 20 minutes to obtain uniform homogeneous pastes. The mixtures were first aged at 45° C. at 30 rpm for 24 hrs. then crystallized at 300° F. (149° C.) in a 2-liter autoclave with stirring at 30 RPM (Example 1) and without stirring (Example 2) for 168 hours (Example 1) or 216 hours (Example 2). After crystallization, the hydrothermal reaction mixture slurries of Examples 1 and 2 were filtered, washed with deionized (DI) water and dried at 250° F. (120° C.). The XRD patterns of the as-synthesized materials (FIG. 3A: Example 1 at 120 hrs; FIG. 3B: Example 1 at 168 hrs, and FIG. 5 for Example 2) shown pure phase MCM-22. The resulting MCM-22 crystals (Examples 1 and 2) had a $SiO_2/Al_2O_3$ molar ratio of about 23.2.

The calcined MCM-22 crystals (Example 1) had a surface area of 629 m²/g. The SEM image (FIG. 4) of the as-synthesized product crystal (Example 1) showed a platelet aggregates morphology with an estimate average platelet diameter of greater than about 2 μm and thickness of 400-500 Å, which is larger as the reference Example A.

The SEM image (FIGS. 6A & 6B) of the as-synthesized product crystals (Example 2) showed a rosette habit morphology with multiple layer plate with an estimate average crystal diameter of greater than about 5 μm and thickness of 400-500 Å, which is larger as the reference Example A.

Examples 3-4

Two hydrothermal reaction mixtures were prepared from water, hexamethyleneimine (HMI) (Sigma-Aldrich Company), silica (Ultrasil™, Degussa Corp.), 45 wt. % sodium aluminate solution, and 50 wt. % sodium hydroxide solution. The mixtures had the following molar compositions as shown in the following Table IXV:

TABLE IXV

|  | Example 3 | Example 4 |
|---|---|---|
| Molar composition | | |
| $SiO_2/Al_2O_3$ | 32 | 30 |
| $H_2O/SiO_2$ | 34 | 21 |
| $OH^-/SiO_2$ | 0.66 | 0.48 |
| $Na^+/SiO_2$ | 0.66 | 0.48 |
| $R/SiO_2$ | 0.15 | 0.15 |
| Crystallization conditions | | |
| Temperature (° C.) | 160 | 160 |
| Stirring speed (RPM) | 30 | 0 |
| Time (hr) | 48, 72 | 72 |
| Characterizations | | |
| XRD Result | See FIG. 7 | See FIG. 9 |
| Crystal size (SEM) | >1 μm × 0.025 μm | >1 μm wide |
| Morphology (SEM | (FIG. 4) | (FIG. 6) |

The above mixtures were well mixed under vigorous stirring for 20 minutes to obtain uniform homogeneous pastes. The mixtures were first aged at 45° C. at 30 rpm for 24 hrs, then crystallized at 300° F. (149° C.) in a 2-liter autoclave with stirring at 30 RPM (Example 3) and without stirring (Example 4) for 168 hours (Example 3) or 216 hours (Example 4). After crystallization, the hydrothermal reaction mixture slurries of Examples 3 and 4 were filtered, washed with deionized (DI) water and dried at 250° F. (120° C.). The XRD patterns of the as-synthesized materials (FIG. 7A: Example 3 at 48 hrs and FIG. 9 for Example 4) shown pure phase MCM-22. The XRD patterns of the as-synthesized material of Example 3 at 72 hrs (FIG. 7B) shown MCM-22 topology with ZSM-35 impurities.

The SEM image (FIG. 8) of the as-synthesized product crystal (Example 3) showed a platelet aggregates morphology with an estimate average platelet diameter of greater than about 2 □m and thickness of 400-500 Å, which is larger as the reference Example A.

The SEM image (FIG. 10) of the as-synthesized product crystals (Example 4) showed a platelet aggregates morphology with an estimate average crystal diameter of greater than about 5 □m, which is larger as the reference Example A.

Example 5

A MCM-22/alumina catalyst was prepared from 80 weight parts of product of Example 1 mixed with 20 weight parts of alumina (Condea SB3) on the dry basis. Water was added to the mixture to allow the resulting catalyst to be formed into ¹⁄₂₀" quadrulobe extrudates. The prepared extrudates were dried at 120° C. before use. The catalyst was activated by calcining in nitrogen at 540° C., followed by aqueous ammonium nitrate exchange and calcining in air at 540° C.

Example 6

Reference Catalyst

A catalyst was prepared from 80 weight parts of product of Example A mixed with 20 weight parts of alumina (LaRoche Versal 300) on a dry basis. The catalyst was slurried in ammonium nitrate, filtered and dried at 120° C. before use. The catalyst was activated by calcining in nitrogen at 540° C., followed by aqueous ammonium nitrate exchange and calcining in air at 540° C.

Example 7

The catalyst from Example 5 was tested in the batch autoclave for liquid phase cumene alkylation. 0.5 grams of the catalyst from Example 5 was loaded into a catalyst basket between two six gram layers of inert quartz. Benzene (156.1 grams) and propylene (28.1 grams) were then added in a 3:1 molar ratio of Benzene:propylene. The reaction conditions were 130° C. at 2183 kPa-a (300 psig) and the reaction was run for 4 hours. Off-line GC was used to monitor the reaction over the 4 hours. The activity and selectivity referenced to the reference catalyst are provided in Table XV below.

TABLE XV

| Catalyst | Activity | Selectivity, normalized [DIPB/Cumene (%)] |
|---|---|---|
| Example 5 | 97 | 119 |

The catalyst showed both activity and selectivity for the benzene alkylation reaction.

While the illustrative embodiments of this disclosure have been described with particularity, it will be understood that various other modifications will be apparent to and can be readily made by those skilled in the art without departing from the spirit and scope of this disclosure. Accordingly, it is not intended that the scope of the claims appended hereto be limited to the Examples and descriptions set forth herein but rather that the claims be construed as encompassing all the features of patentable novelty which reside in the present invention, including all features which would be treated as equivalents thereof by those skilled in art to which this disclosure pertains.

We claim:

1. A crystalline MCM-22 family molecular sieve having, in its assynthesized form, a platelet aggregates morphology wherein greater than 50 wt % of the molecular sieve having a crystal with a diameter greater than 1 μm and a thickness of about 0.04 μm as measured by the SEM.

2. The crystalline MCM-22 family molecular sieve of claim 1, wherein the platelet aggregates morphology is rosette habit morphology.

3. The crystalline MCM-22 family molecular sieve of claim 1, wherein the crystal of the molecular sieve comprises multiple sub-crystal plates.

4. The crystalline MCM-22 family molecular sieve of claim 1, wherein greater than 50 wt % of the molecular sieve having a crystal diameter greater than 2 μm as measured by the SEM.

5. The crystalline MCM-22 family molecular sieve of claim 1, wherein greater than 50 wt % of the molecular sieve having a crystal diameter greater than 5 μm as measured by the SEM.

6. The crystalline molecular sieve of claim 1, having a total surface area of greater than 450 m²/g as measured by the N₂ BET method.

7. A method of manufacturing the crystalline MCM-22 family molecular sieve of claim 1, comprising:
   (a) combining at least one silicon source, at least one source of at least one alkali or alkali earth metal element, at least one directing-agent (R), water, and optionally at least one aluminum source, to form a mixture having the following mole composition:

| | |
   |---|---|
   | Si:Al₂ = | 10 to infinity |
   | H₂O:Si = | 1 to 10000 |
   | OH⁻:Si = | 0.001 to 2 |
   | M⁺:Si = | 0.001 to 2 |
   | R:Si = | 0.001 to 2 | wherein M is an alkali metal and R is selected from the group consisting of cyclopentylamine, cyclohexylamine, cycloheptylamine, hexamethyleneimine, heptamethyleneimine, homopiperazine, and combinations thereof;
   (b) submitting the mixture at crystallization conditions to form a product comprising the desired crystalline molecular sieve, wherein the crystallization conditions comprise a temperature in the range of from 100° C. to 250° C., a crystallization time from about 1 hour to 200 hours; and optionally a stirring speed in the range of from 0 to less than about 60 RPM; and
   (c) recovering the molecular sieve.

8. The method of claim 7, wherein the R is hexamethyleneimine.

9. The method of claim 7, wherein the temperature is in the range of about 150 to 180° C.

10. The method of claim 7, wherein the stirring speed is less than 30 RPM.

11. The method of claim 7, wherein the silicon source is silicic acid.

12. The method of claim 7 wherein the silicon source is silica.

13. A process for hydrocarbon conversion, comprising the step of:
   (a) contacting a hydrocarbon feedstock with a crystalline MCM-22 family molecular sieve, said crystalline MCM-22 family molecular sieve having, in its as-synthesized form, a platelet aggregates morphology wherein greater than 50 wt % of the molecular sieve having a crystal with a diameter greater than 1 μm and a thickness of about 0.04 μm as measured by the SEM, under conversion conditions to form a conversion product.

14. A method of manufacturing the crystalline MCM-22 family molecular sieve, said crystalline MCM-22 family molecular sieve having, in its assynthesized form, a platelet aggregates morphology wherein greater than 50 wt % of the molecular sieve having a crystal diameter greater than 1 μm as measured by the SEM, the method comprising the steps of:
   (a) providing a mixture comprising at least one source of at least one tetravalent element (Y), at least one source of at least one alkali or alkali earth metal element, at least one directing-agent (R), water, and optionally at least one source of at least one trivalent element (X), said mixture having the following molar composition:
   Y:X₂=10 to infinity
   H₂O:Y=1 to 10000
   OH⁻:Y=0.001 to 2
   M⁺:Y=0.001 to 2
   R:Y=0.001 to 2
      wherein M is an alkali metal and R is selected from the group consisting of cycloalkylamine, azacycloalkane, diazacycloalkane, and mixtures thereof, wherein said alkylamine or alkane comprises from 5 to 8 carbon atoms;
   (b) submitting the mixture at crystallization conditions to form a product comprising the desired crystalline molecular sieve, wherein the crystallization conditions comprise a temperature in the range of from 100° C. to 250° C., a crystallization time from about 1 hour to 200 hours; and optionally a stirring speed in the range of from 0 to less than about 60 RPM; and
   (c) recovering the molecular sieve.

15. The method of claim 14, wherein the tetravalent element is silicon.

16. The method of claim 14, wherein the trivalent element is aluminum.

17. The method of claim 14, wherein the R includes cyclopentylamine, cyclohexylamine, cycloheptylamine, hexamethyleneimine, heptamethyleneimine, homopiperazine, and combinations thereof 18. The method of claim 14, wherein the R is hexamethyleneimine.

19. The method of claim 14, wherein the temperature is in the range of about 150 to 180° C.

20. The method of claim 14, wherein the stirring speed is less than 30 RPM.

21. The method of claim 14, wherein the stirring speed is less than 15 RPM.

22. The method of claim 14, wherein the tetravalent element source is silicic acid.

23. The method of claim 14, wherein the tetravalent element source is silica.

24. The method of claim 14, further comprising a step of forming catalyst particulates by at least one of spray drying, prilling, pelletizing, and/or extrusion.

* * * * *